(12) United States Patent
French

(10) Patent No.: US 7,699,820 B1
(45) Date of Patent: Apr. 20, 2010

(54) DEVICE FOR IRRIGATING THE EAR CANAL

(76) Inventor: Ronald J. French, 6123 Marquette Pl., New Orleans, LA (US) 70118

( * ) Notice: Subject to any disclaimer, the term of this patent is extended or adjusted under 35 U.S.C. 154(b) by 13 days.

(21) Appl. No.: 12/189,996

(22) Filed: Aug. 12, 2008

(51) Int. Cl.
*A61M 31/00* (2006.01)
*A61M 1/00* (2006.01)
*A61M 37/00* (2006.01)

(52) U.S. Cl. .................. 604/275; 604/35; 604/150
(58) Field of Classification Search ......... 604/275–279, 604/35–39
See application file for complete search history.

(56) References Cited

U.S. PATENT DOCUMENTS

| 4,201,212 | A | * | 5/1980 | Bradley ................ 604/346 |
| 4,206,756 | A | | 6/1980 | Grossan |
| 4,282,867 | A | | 8/1981 | Tu Toit |
| 5,241,714 | A | | 9/1993 | Barry |
| 5,309,899 | A | * | 5/1994 | Ginsberg ................ 604/38 |
| 5,685,851 | A | | 11/1997 | Murphy et al. |
| 5,833,675 | A | | 11/1998 | Garcia |
| 6,458,094 | B1 | | 10/2002 | McMahon et al. |
| 6,485,451 | B1 | * | 11/2002 | Roberts et al. ........... 604/35 |
| 6,875,196 | B2 | | 4/2005 | Abita et al. |
| 7,273,467 | B1 | | 9/2007 | Mezzoli |
| 7,361,170 | B2 | | 4/2008 | Williams et al. |
| 2006/0253087 | A1 | | 11/2006 | Vlodaver et al. |
| 2008/0111283 | A1 | * | 5/2008 | Espersen et al. ........... 264/401 |

* cited by examiner

*Primary Examiner*—Kevin C Sirmons
*Assistant Examiner*—Imani Hayman
(74) *Attorney, Agent, or Firm*—Carvey, Smith, Nehrbass & North, L.L.C.; Gregory C. Smith

(57) ABSTRACT

A device for irrigating cerumen from one's ear canal, which includes a universal adaptor affixed to the spout of a lavatory faucet (one which allows the cold and hot to be mixed); a flow line extending from the adaptor; a valve on the adaptor, which when opened allows for adjusting the temperature and force of flow by feeling the flow at a nozzle on the second end of the flow line; a cup for placement over the ear to contain the water flow; a double loop within the cup to mount a first loop to a tragus portion of the outer ears for directing fluid flow from the nozzle into the ear canals, a second loop engaged around a probe to limit the depth the nozzle is able to enter the ear canal; and a return line for returning water and debris collected from the ear canal into the lavatory.

10 Claims, 5 Drawing Sheets

DEVICE FOR IRRIGATING THE EAR CANAL

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a device for irrigating and cleaning the ear canal. More particularly, the present invention relates to a device which includes a flow line which connects to a water source, such as a faucet, on a first end, and terminates in a nozzle on the second end, the nozzle contained within a cup engaged over the outer ear, allowing water to flow from the faucet through the flow line and exit the nozzle, the water directed into the ear canal under pressure, and returned to a basin through a return flow line.

2. General Background

In the process for cleaning the ear canal of a person, many different methods for home treatment have been tried, both various kinds of drops as well as methods of irrigation or flushing. Ultimately many need medical help, and most often by an ear specialist. In the most common method of simply forcing water from a syringe or bulb into the ear canal provides a limited amount of water, and when the water fills the canal, the water simply drains out of the ear onto the person or the surrounding area. Therefore, there is a need for a system which allows a person to inject a controlled flow of water into ones ear, at a desired temperature, and when the water flows from the ear, it is collect at the ear and returned to a basin or the like through a collection line.

The following U.S. patents are incorporated herein by reference:

TABLE

| PATENT NO. | TITLE | ISSUE DATE |
| --- | --- | --- |
| U.S. Pat. No. 4,206,756 | Jet Ear Irrigation System | Jun. 10, 1980 |
| U.S. Pat. No. 4,282,867 | Cleaning Fluid Injection Device | Aug. 11, 1981 |
| U.S. Pat. No. 5,241,714 | Shower Person Hygiene System | Sep. 7, 1993 |
| U.S. Pat. No. 5,685,851 | Irrigation Syringe | Nov. 11, 1997 |
| U.S. Pat. No. 5,833,675 | Irrigator Device | Nov. 10, 1998 |
| U.S. Pat. No. 6,458,094 | Disposable Tip for Body Cavity Irrigation System | Oct. 1, 2002 |
| U.S. Pat. No. 6,485,451 | Body Cavity Irrigation System | Nov. 26, 2002 |
| U.S. Pat. No. 6,875,196 | Vestibular Irrigation Test System | Apr. 5, 2005 |
| U.S. Pat. No. 7,273,467 | Device For Washing The External Auditory Meatus | Sep. 25, 2007 |
| U.S. Pat. No. 7,361,170 | Device, System, Kit or Method For Collecting Effluent From An Individual | Apr. 22, 2008 |
| 20060253087 | Medication Delivery Device | Nov. 9, 2006 |

SUMMARY OF THE PRESENT INVENTION

The present invention solves the problems in the art in a simple and straightforward manner. What is provided is a device which allows one to irrigate the cerumen or wax from his ear canal. What is provided is a universal adaptor is affixed to the spout of a bathroom lavatory faucet (one which allows the cold and hot to be mixed); a flow line extending from the adaptor; a valve on the adaptor, which when opened allows one to adjust the temperature by feeling the flow at a nozzle on the second end of the flow line; a cup for placement over the ear to contain the water flow; a double loop within the cup to mount a first loop to a tragus portion of the outer ears for directing fluid flow from the nozzle into the ear canals, and a second loop engaged around a probe to limit the depth the nozzle is able to enter the ear canal; and a return line for returning the water and any debris collected from the ear canal into the lavatory.

In operation, the cup is placed over ear to contain water, and the head is tilted over the basin. The nozzle enters the cup via a flexible membrane which allows one to both point and move the nozzle into the ear canal entry. The Valve is opened as fully as required to provide the force for flushing debris out of the ear canal. The flushing activity continues until the ear feels clear or the user wants to check the collection. The water flows into the basin via the return flow line. A cover at end of the return flow line would include a screw off screen, so one may observe the return from the irrigation, as well as clean the screen.

Therefore, it is a principal object of the present invention to allow one to perform the task of cleaning one's own ears, in a tidy, efficient and painless fashion. Since water colder or warmer than that of body temperature will give vertigo, it is important that one may set the correct temperature for the water.

It is a further object of the present invention to provide a means to vary the water pressure directed into the ear to control the force required to flush impacted cerumen, as well as for comfort, that control is afforded.

It is a further object of the present invention to provide a mechanism for allowing water, at a desired temperature, to flow into the ear canal, at a controlled force, to clean the canal and to return the water to a basin or lavatory, without escaping into the surrounding area or onto the person.

It is a further object of the present invention to provide a mechanism for cleaning the ear canal including a structure to allow a probe and nozzle to be inserted into the ear, but only to a predetermined depth so as to avoid damage to the ear canal, yet provide a means to manipulate the nozzle inject water for proper cleaning of the ear canal.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE PREFERRED EMBODIMENT

Figure 1:
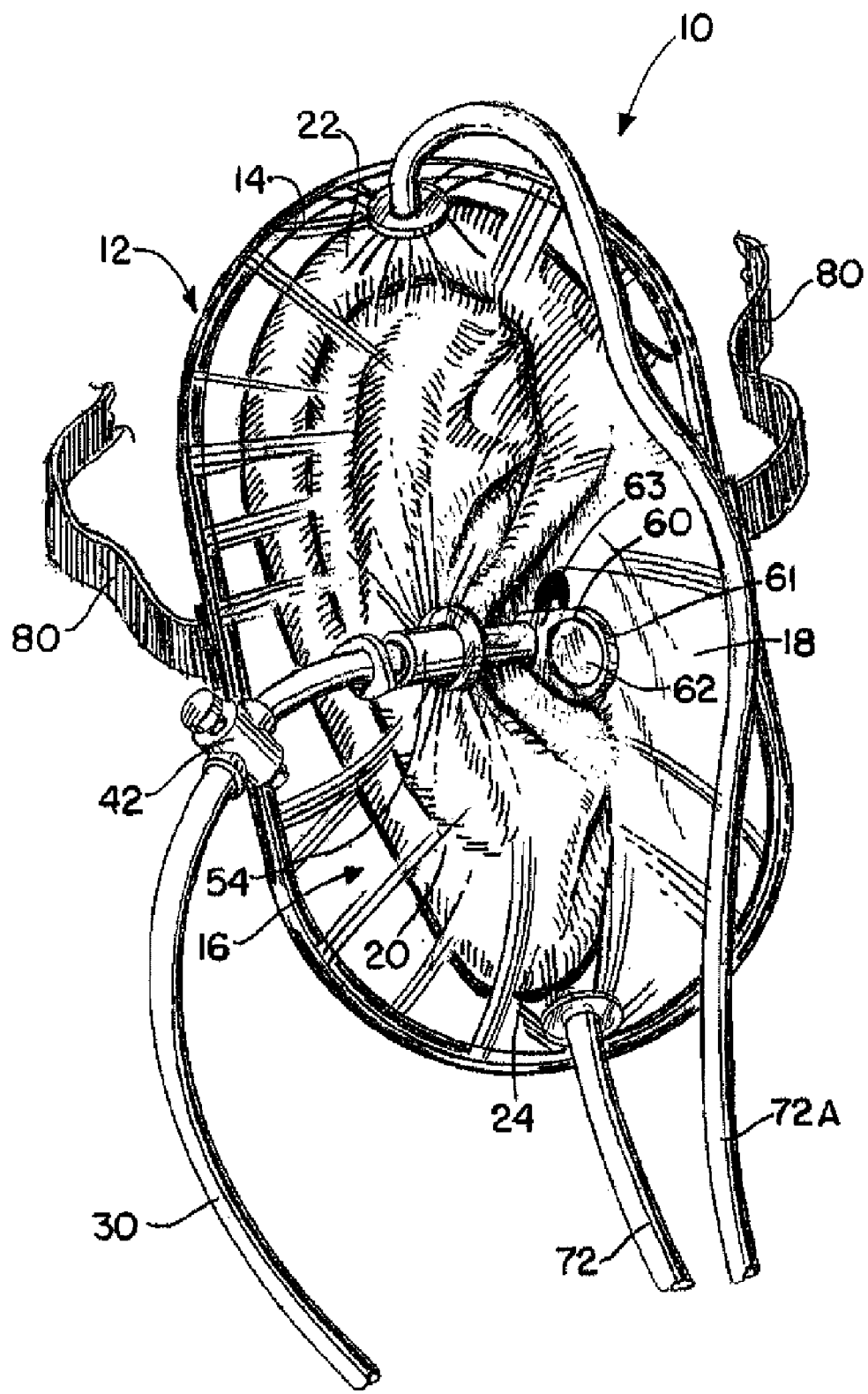
FIG. 1 is an overall view of the cleaning system for the ear canal mounted on the earlobe.

FIGS. 1-6 illustrate the preferred embodiment of the device of the present invention by the numeral 10. As seen in FIG. 1, there is illustrated a substantially oval cup portion 12 having an outer rim 14 and a flexible body portion 16. The body portion 16 would include a flexible, substantially transparent membrane 18 secured around the edge 14, to define the oval cup portion 12. As seen in operation in FIGS. 1 and 5, oval cup 12 is of sufficient size to cover a human outer ear 20, extending from the helix portion 22 down to the lobule portion 24, with the outer rim 14 pressed against the flat surface 17 of the skull 19 surrounding the outer ear 20, so that the rim 14 would capture fluid, such as water, that would be entering the cup member 12 during operation.

Figure 2:
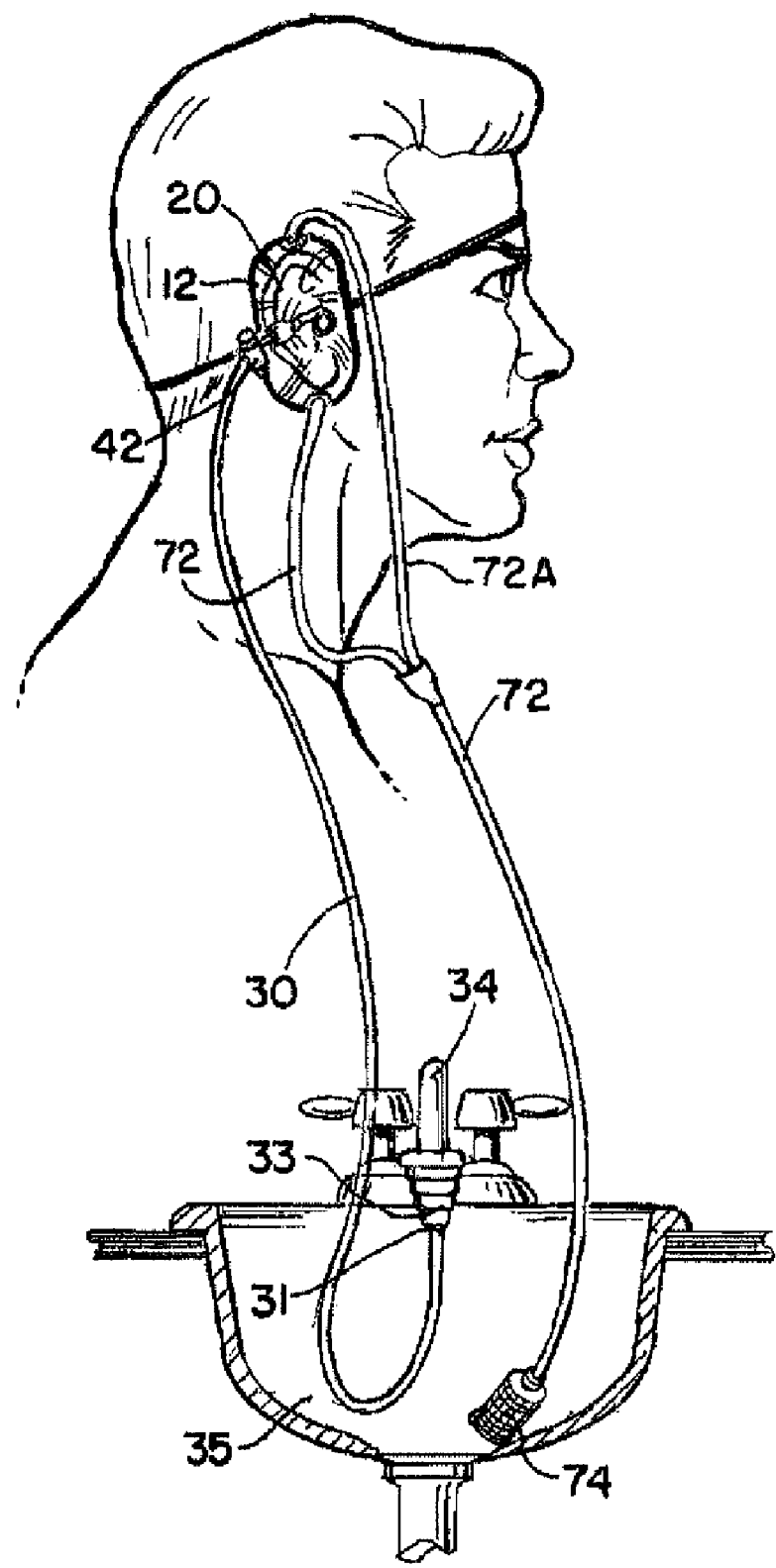
FIG. 2 is an overall illustration of the system mounted on the earlobe showing the input and drain lines directed from the water source.
Figure 3:
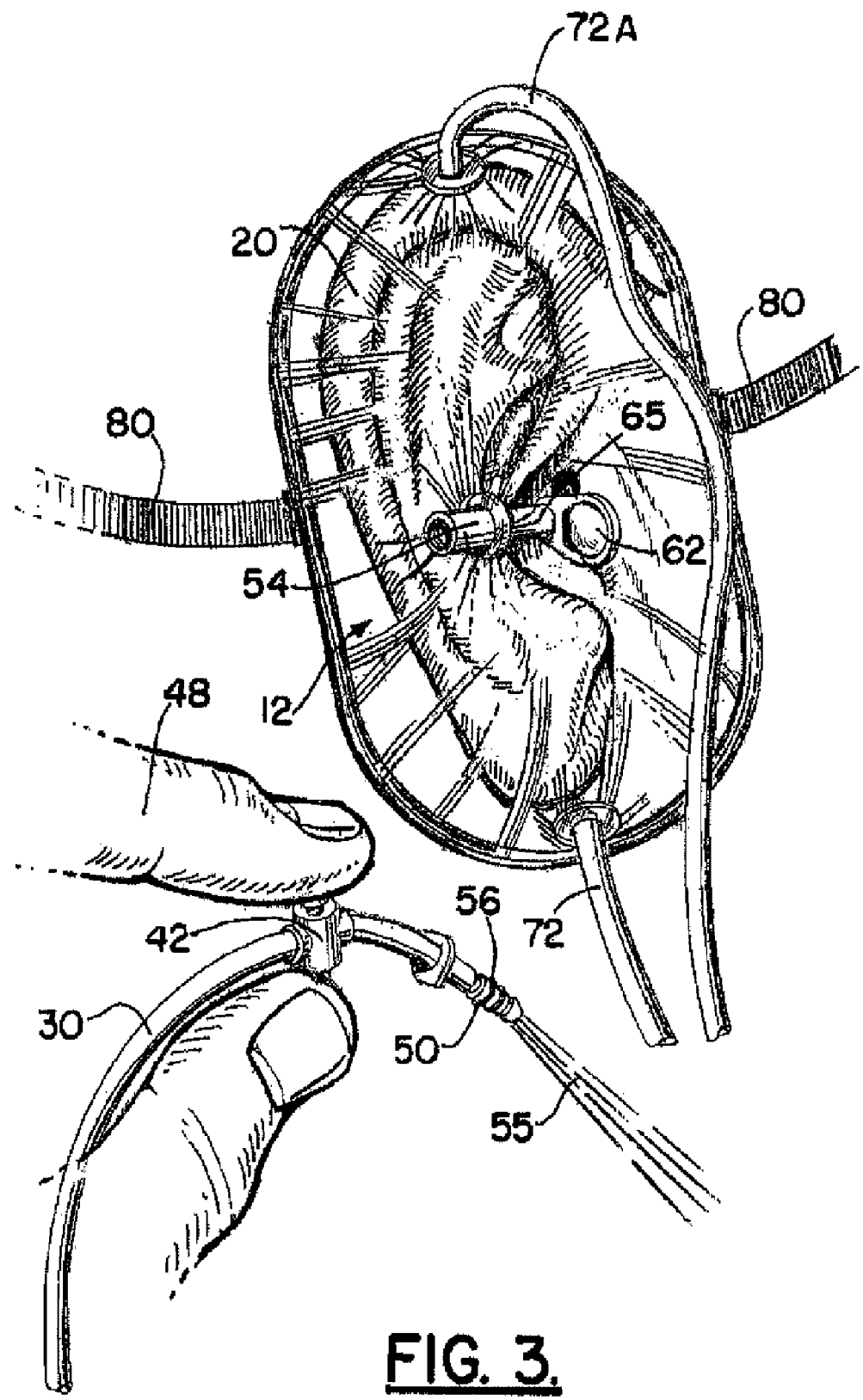
FIG. 3 is a broad view of the system of the invention mounted on the earlobe illustrating in partial view the valve member secured to the end of the line.
Figures 5, 6:
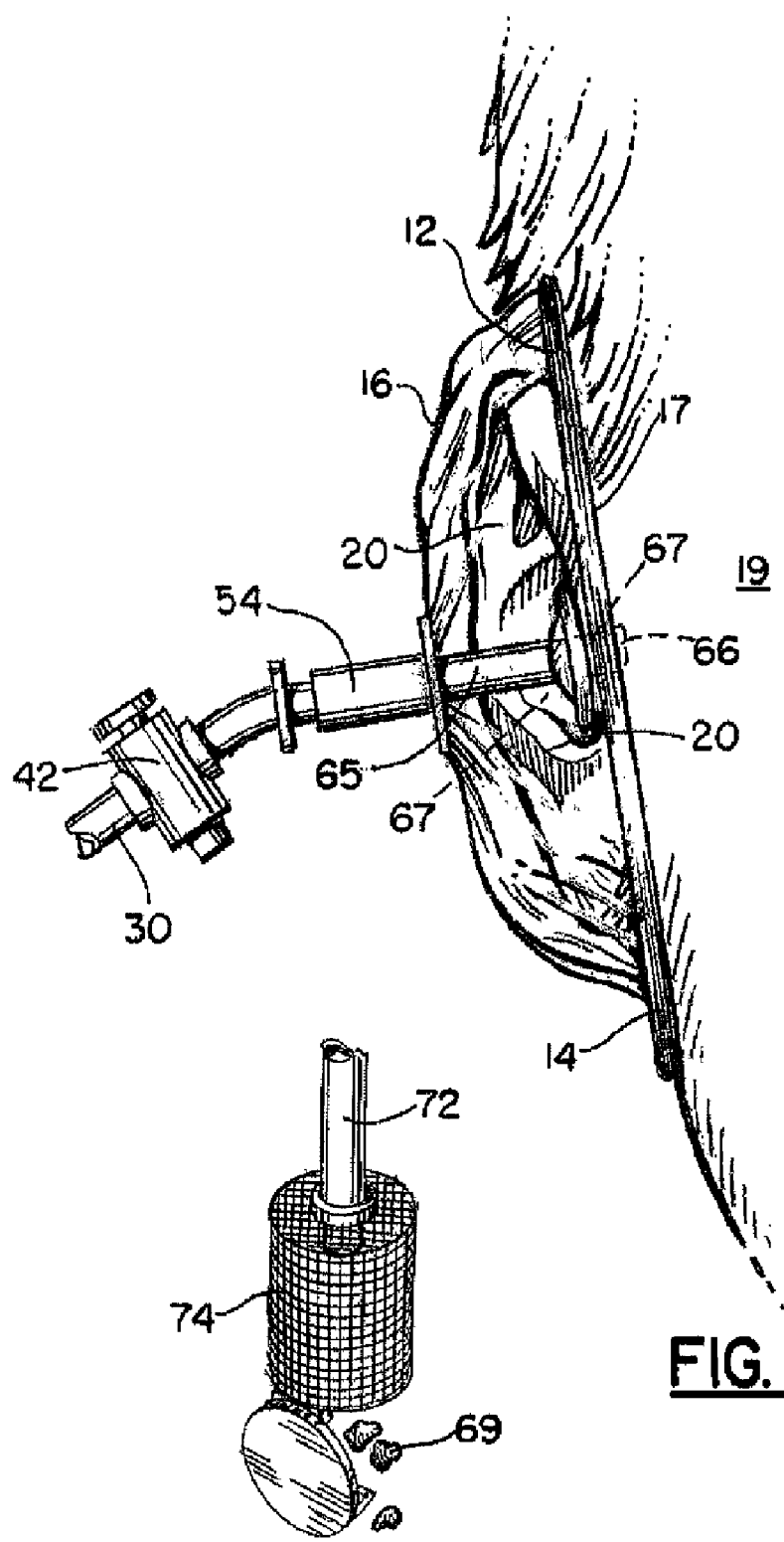
FIG. 5 is a side cut-away view of the nozzle portion of the system engaged into the ear cover during operation.
FIG. 6 is a view of the filter member which is secured to the end of the drain line to capture debris (such as cerumen and wax) that has been washed from the ear for further viewing.

Further, as seen in partial view in FIG. 1 and in full view in FIG. 2, the cup member 12 includes a first fluid flow line 30 which is adapted at a first end 31 to an adaptor 33 on faucet 34, as part of a lavatory face basin 35, so that line 30 can receive a mixture of both cold and hot water from faucet 34. Of course, if the face basin 35 has dual faucets 34, for hot and cold, the line 30 could be branched off to both faucets 34 and mixed through line 30 before the water reaches the cup member 12. In either configuration, in order to get the proper mixture of hot and cold water, for the desired temperature, the water flowing in flow line 30 from faucet 34 would encounter a valve 42, which is seen more in detail view in FIG. 1. Valve 42 is a valve that can be manipulated manually by the user's hand 48, as seen in FIG. 3, to adjust both the temperature of the water and the force of the water entering cup member 12. As seen in FIG. 3, line 30 has a quick connect fixture 50 at its end portion, which would be secured to an adaptor 54 on the cup member 12. Adaptor 54 would terminate at a probe 65 engaged at its end to a nozzle portion 66 within the ear canal 67, as seen in FIG. 5. To set the temperature and force of the water flowing in line 30, the quick connector 50 would be disengaged from adaptor 54, so that the user could feel the temperature of the water 55 flowing out of the end 51 of fixture 50. When the desired temperature is set, the fixture 50 would be re-engaged into adaptor 54, to form a fluid tight seal via o-rings 56. As seen in FIG. 5, the valve 42 would be open to allow water 55 to flow into cup member 12, through probe 65, and out of nozzle 66 and into the ear canal 67, as will be described further.

After the quick connect fixture 50 has been re-engaged into adaptor 54, reference is made to FIGS. 1 and 2. As illustrated, positioned on fixture 54, within cup member 12, there is a loop 60 configured in a "Figure eight", which would have a first loop 61 in the figure eight loop positioned to engage around the tragus 62, of the outer ear 20, the tragus 62 being the small projection just in front of the ear canal 67. The second loop 63 of the figure eight loop 60 would secure the probe 65 for introducing water into the ear canal 67, and insure that the nozzle 66 would not be forced into the ear canal 67 beyond a certain depth. This feature provides that the nozzle 66 is properly directed into ear canal 67 as water flow would commence. In FIG. 3, after figure eight loop 60 has been engaged onto tragus 62, valve 42 is opened and water would then flow through adaptor 54 and through and out of nozzle 66, secured in loop 63, as seen in FIG. 5, in order to enter the ear canal 67 and flush any debris 69 (such as cerumen and wax) out of the canal 67. It is important to note that the cup member 12 would be made of a flexible material, so that the nozzle portion 66 would not be rigidly fixed within the ear canal 67 but could be manually manipulated on the exterior of the surface of the cup member 12 so as to make certain that the cleaning is complete during the process. This is seen in phantom view in FIG. 4, where a user's hand 48 has reached and is manipulating the probe 65 to move the nozzle member 66 in a certain direction to confirm that the cleaning has been completed.

Figure 4:
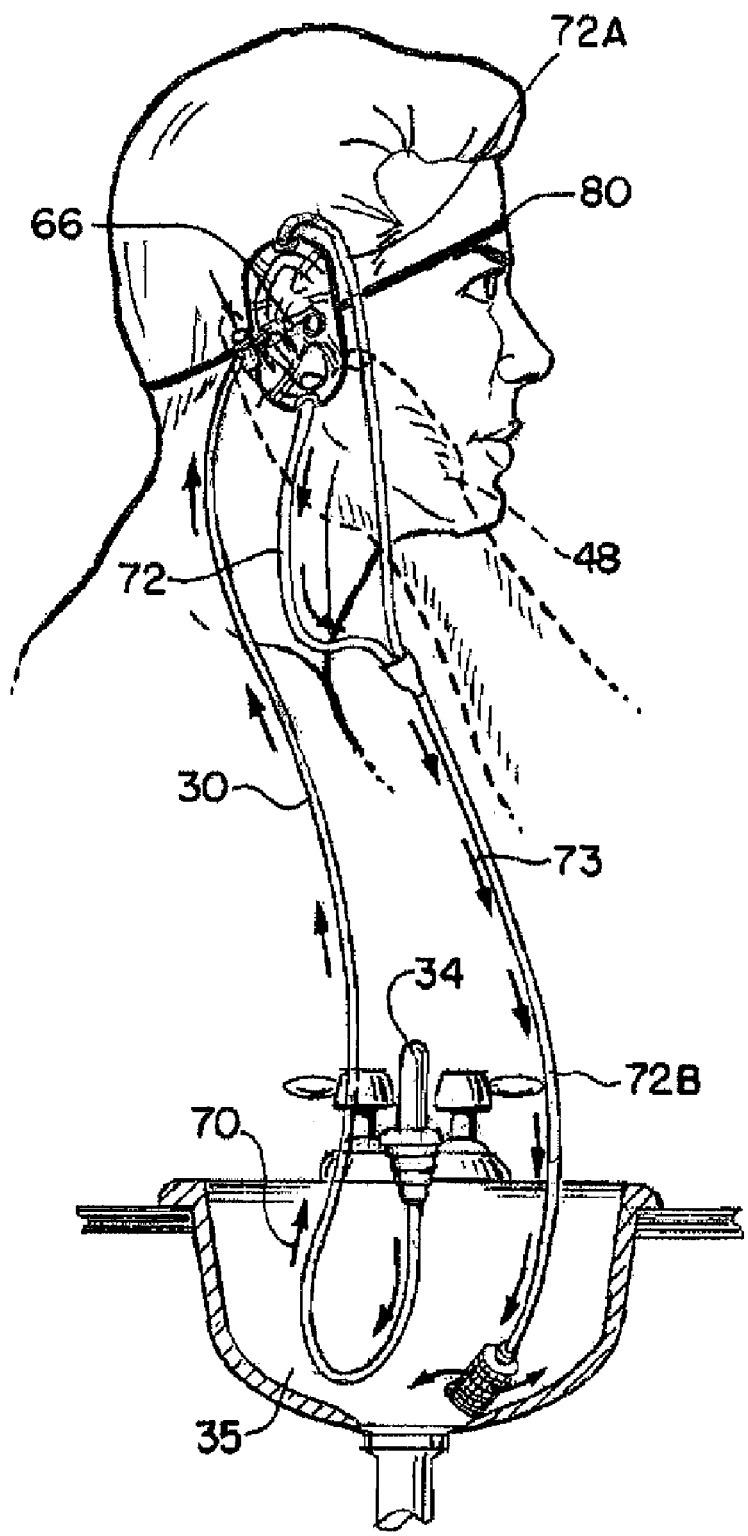
FIG. 4 is a view similar to FIG. 2 showing the flow of water into an out of the fixture on the earlobes.

During the cleaning process, water is continuing to flow into the cup member 14 through line 30. FIG. 4 illustrates the flow of the water moving in the direction of arrow 70 from faucet 34. In order to allow a constant flow of fresh water into the cup during the cleaning process, there is provided a first exit flow line 72. As the water flows into the ear canal 67, the excess water then would be drained off via exit flow line 72, in the direction of arrow 73, and would return from down line 72 to encounter a trap 74, set within basin 35, which allows water to flow into the basin 35, but would catch any debris 69 therein as seen in FIG. 6, when the trap 74 is open.

As seen further in FIG. 4, there is a second exit flow line 72A, which in the Figure is exiting from the upper portion of the cup member 12. As seen in FIG. 4, the device 10 is mounted on the right outer ear 20 of a person. When the device 10 is shifted to the left outer ear 20, the device would be rotated 180 degrees so that the cup member 12 may engage the left outer ear 20 in the same manner as was described above. Because line 72A would be then extending from the bottom of the cup member 12 once it has been rotated to be affixed to the left ear, the second line 72A would become the primary exit flow line, and join line 72 to flow into the basin 35.

It should be seen that there is provided a flexible band 80 extending from the cup member 12, the band 84 wrapped around a person's head in order to secure the device 10 in place during the use of the device in the cleaning process. Of course, when the cleaning process is complete, the valve 42 may be shut off and the device removed from one ear and placed on the other ear 20, with the loop engaging the tracheas and then the process would be resumed.

In conclusion, the present invention allows one to irrigate the cerumen or wax from one's ear canal. Many different methods of home treatment have been tried, both various kinds of drops as well as methods of irrigation or flushing. These devices have not been successful, and medical attention is usually required, most often by an ear specialist, if one is available. This apparatus allows one to perform the task on oneself, in a tidy and painless fashion.

Flushing the ear canal must be done with water of body temperature. Failing to do this will cause dizziness or vertigo in the patient. For this reason the temperature of the water must be tested after regulation, but before directing it into the ear. Trying to adjust the stream of water while it is flowing into the ear could cause discomfort or damage. This device has a connection which can be made onto the ear irrigation system after temperature adjustment.

Water pressure must be variable for comfort and safety. It is likewise injudicious to regulate the pressure while the stream is coursing in the ear canal. The above mentioned connection allows both the temperature and pressure be checked in the line of the system the before the ear canal is entered.

Introduction of a probe into the ear canal may be dangerous and may produce injury to the ear or ear drum. If one is irrigating his own ear, it is necessarily done so blindly. If another is doing the irrigation, he cannot see beyond the probe and waster stream into the canal for safety.

In summary, this device, uniquely, includes a loop 60 adjacent to the end of the water jet introducing probe 66. This loop fits over the tragus 62, which is the protuberance in front of the ear canal 67, allowing (a) limitation of instrumentation into the ear canal, avoiding possible internal damage; (b) traction the loop in forward direction opens the canal widely for introduction of the irrigating stream of water; and (c) direction of the water jet in the varying directions of individual ear canals is afforded by the fulcrum of the loop/probe complex.

In the preferred method of use, as explained fully above, a universal adaptor is affixed to the spout of a bathroom lavatory faucet (one which allows the cold and hot to be mixed), or shower nozzle. The water is turned on and valve a is opened, allowing one to adjust the temperature and pressure by feeling the flow at the nozzle. Tube for return is placed in the lavatory. Cup is placed over ear to contain water, and head is tilted over the basin. The valve is closed allowing the nozzle is attached to the probe which will direct the flow into the ear canal. There is a loop making a figure eight configuration with the probe end. The loop is placed over the tragus. The tragus is the protuberance in front of the ear canal. As the valve is opened allowing the jet stream begin entering the ear canal, the probe/loop complex can be moved to fully open the ear canal, and to direct the stream in the direction of the individual canal. The probe facilitates this movement as its fixation to the ear cup covering is with a somewhat flexible membrane. After flushing the canal the cerumen obtained can be examined and discarded from the screen at the end of the waste line.

The following is a list of suitable parts and materials for the various elements of the preferred embodiment of the present invention.

PARTS LIST

| Description | Part Number |
| --- | --- |
| device | 10 |
| oval cup portion | 12 |
| outer rim | 14 |
| body portion | 16 |
| surface | 17 |
| flexible membrane | 18 |
| skull | 19 |
| outer ear | 20 |
| helix portion | 22 |
| lobule portion | 24 |
| first flow line | 30 |
| first end | 31 |
| adaptor | 33 |
| faucet | 34 |
| face basin | 35 |
| valve | 42 |
| user's hand | 48 |
| quick connect fixture | 50 |
| adaptor | 54 |
| water | 55 |
| o-rings | 56 |
| circular loop | 60 |
| first figure eight loop | 61 |
| second figure eight loop | 63 |
| tragus | 62 |
| probe | 65 |
| nozzle | 66 |
| ear canal | 67 |
| debris | 69 |
| arrow | 70 |
| exit flow line | 72 |
| exit flow line | 72A |
| arrow | 73 |

-continued

PARTS LIST

| Description | Part Number |
| --- | --- |
| trap | 74 |
| flexible band | 80 |

All measurements disclosed herein are at standard temperature and pressure, at sea level on Earth, unless indicated otherwise. The foregoing embodiments are presented by way of example only; the scope of the present invention is to be limited only by the following claims.

The invention claimed is:

1. A device for cleaning cerumen and wax from a human ear canal, comprising:
   a. a fluid flow line, having a first end attachable to a faucet and a second end terminating in a nozzle portion;
   b. a cup positionable around an outer ear, having an opening through which the nozzle protrudes into an ear canal;
   c. loop means positioned on the nozzle portion to mount the nozzle portion to a tragus portion of the outer ear in order to limit the depth of the nozzle into the ear canal to avoid damage to the ear canal and eardrum, and for allowing the manipulation of the nozzle portion to direct sufficient fluid flow from the nozzle into the length of the ear canal to clean the canal;
   d. a first return fluid flow line extending from the cup and terminating at a point away from the person during cleaning of a first ear canal; and
   e. a second return fluid flow line for providing fluid flow out of the cup when cleaning a second ear canal.

2. The device in claim 1, further comprising a valve for regulating the flow and temperature of water from the faucet to the nozzle.

3. The device in claim 1, further comprising an adaptor for allowing the flow line to be secured to the faucet.

4. The device in claim 1, wherein the loop means comprises a double loop, with a first loop engaged around a tragus structure on the outer ear and a second loop engaged around a probe securing the nozzle.

5. The device in claim 1, wherein the fluid flow line from the faucet to the cup includes a quick connect for engaging and disengaging the flow line to the cup during the cleaning process.

6. A device attachable to first and second outer ears for irrigating and cleaning cerumen and wax from ear canals, comprising:
   a. a fluid flow line, having a first end attachable to a faucet and a second end terminating in a nozzle portion;
   b. a cup positionable around the outer ears, having an opening through which the nozzle protrudes into the ear canals;
   c. a double loop positioned on the nozzle portion to mount a first loop to a tragus portion of the outer ears for directing fluid flow from the nozzle into the ear canals, and a second loop engaged around a probe to limit the depth the nozzle is able to enter the ear canal;
   d. a first return fluid flow line extending from the cup and terminating at a point away from the person during cleaning of the first ear canal; and
   e. a second return fluid flow line extending from the cup to provide fluid flow out of the cup and terminating at a point away from the person during cleaning of the second ear canal.

7. The device in claim 6, further comprising a valve for regulating the flow and temperature of water from the faucet to the nozzle.

8. The device in claim 6, further comprising an adaptor for allowing the flow line to be secured to the faucet.

9. A device for cleaning cerumen and wax from an ear canal of a human ear, comprising:
   a. a flexible cup positionable around an outer ear, including an adaptor for receiving fluid flow into the cup;
   b. a fluid flow line, having a first end attachable to a faucet and a second end connecting to the adaptor;
   c. a nozzle secured to the adaptor within the cup and protruding into the ear canal;
   d. a loop secured to the adaptor within the cup to mount the nozzle to a tragus portion of the outer ear for directing the fluid flow from the nozzle into the ear canal and for limiting the depth of the nozzle into the ear canal;
   e. a first return fluid flow line extending from the cup and terminating at a point away from the person during cleaning of a first ear canal; and
   f. a second return fluid flow line for flowing water from the cup when the cup is placed on a second ear, and the cup is rotated 180 degrees.

10. A device for cleaning cerumen and wax from a human ear canal, comprising:
   a. a fluid flow line, having a first end attachable to a faucet and a second end terminating in a nozzle portion;
   b. a cup positionable around the outer ears, having an opening through which the nozzle portion protrudes into the ear canals;
   c. a loop means positioned on the nozzle portion to mount the nozzle to a tragus portion of the outer ear to limit the depth of the nozzle into the ear canal in order to avoid damage to the ear canal and eardrum, and for allowing the manipulation of the nozzle portion to direct sufficient fluid flow from the nozzle into the length of the ear canal to clean the canal;
   d. a first return fluid flow line extending from the cup and terminating at a point away from the person during cleaning of a first ear canal; and
   e. a second return fluid flow line for flowing water from the cup when the cup is placed on a second ear, and the cup is rotated 180 degrees.

* * * * *